(12) United States Patent
De Ridder

(10) Patent No.: US 10,155,114 B2
(45) Date of Patent: Dec. 18, 2018

(54) SYSTEMS AND METHODS OF TREATING A NEUROLOGICAL DISORDER IN A PATIENT

(71) Applicant: Dirk De Ridder, Dunedin (NZ)

(72) Inventor: Dirk De Ridder, Dunedin (NZ)

(*) Notice: Subject to any disclaimer, the term of this patent is extended or adjusted under 35 U.S.C. 154(b) by 0 days.

(21) Appl. No.: 14/728,726

(22) Filed: Jun. 2, 2015

(65) Prior Publication Data

US 2015/0343215 A1 Dec. 3, 2015

Related U.S. Application Data

(60) Provisional application No. 62/007,058, filed on Jun. 3, 2014.

(51) Int. Cl.
*A61N 1/36* (2006.01)

(52) U.S. Cl.
CPC ..... *A61N 1/36025* (2013.01); *A61N 1/36082* (2013.01)

(58) Field of Classification Search
CPC .............. A61N 1/36082; A61N 1/0531; A61N 1/0534; A61N 1/0529; A61N 1/36025; A61N 1/3606; A61N 1/0456; A61N 1/3605; A61N 1/36089; A61N 1/32; A61N 1/0526; A61N 1/00; A61N 1/08; A61N 1/18; A61N 1/36; A61N 1/36139; A61N 2001/36039; A61M 2205/054; A61B 5/4064; A61B 5/4848; A61B 5/02; A61B 5/0476; A61B 5/0478; A61B 5/165
See application file for complete search history.

(56) References Cited

U.S. PATENT DOCUMENTS

| | | | | |
|---|---|---|---|---|
| 6,463,328 B1 * | 10/2002 | John | .................. | A61N 1/36135 607/45 |
| 7,493,171 B1 * | 2/2009 | Whitehurst | ....... | A61M 5/14276 128/898 |
| 8,315,703 B2 * | 11/2012 | Lozano | .............. | A61N 1/36082 607/45 |
| 2014/0257430 A1 | 9/2014 | Kilgard et al. | | |

OTHER PUBLICATIONS

International Search Report dated Nov. 2, 2015—PCT Application No. PCT/US 15/0033976.

* cited by examiner

*Primary Examiner* — Deborah Malamud

(57) ABSTRACT

In embodiments of the present disclosure, methods of treating a neurological disorder comprise providing reconditioning electrical stimulation. The methods may comprise applying electrical stimulation that provides positive reinforcement by activation within the reward network of the brain of the patient when an appropriate external stimulus is provided to the patient. The external stimulus is selected in accordance with the specific neurological disorder being treated in the patient. The methods may comprise applying electrical stimulation that provides negative reinforcement by stimulation of aversion-related locations of the brain of the patient when a different external stimulus is provided to the patient.

27 Claims, 6 Drawing Sheets

SYSTEMS AND METHODS OF TREATING A NEUROLOGICAL DISORDER IN A PATIENT

This application claims the benefit of U.S. Provision Patent Application Ser. No. 62/007,058, filed Jun. 3, 2014, entitled "METHODS OF TREATING A NEUROLOGICAL DISORDER IN A PATIENT," which is incorporated herein by reference.

BACKGROUND

Drug addiction is typically characterized by two features, a craving or compulsion to take the drug and an inability to limit intake of the drug. Additionally, drug dependence is associated with tolerance, which is the loss of effect of the drug with repeated administration and withdrawal, defined as the appearance of physical and behavioral symptoms when the drug is not consumed following chronic use. Sensitization occurs if the repeated administration of a drug leads to an increased response to each dose. Tolerance, sensitization, and withdrawal are phenomena reflecting some sort of plastic change occurring in the central nervous system in response to continued use of a substance. Drug addiction is related to allostasis, i.e. a resetting of the homeostatic set point or reference around which normal fluctuations occur.

Researchers in the field of drug dependence and reward have identified neurological substrates involved in animal motivation and reward and how the neural mechanisms of these substrates are engaged to result in an addictive state (George F. Koob, "Drugs of abuse: anatomy, pharmacology and function of reward pathways," TiPS—May 1992 [Vol. 13]). The mesolimbic dopamine system which innervates the nucleus accumbens has been determined to be the portion of the brain which plays a critical role in mediation of the reinforcing aspects of addiction and the reinforcing aspects of withdrawal. In 1954, Olds and Milner demonstrated the reward circuits of the brain by electrical stimulation of the septal area of the brain ("Positive reinforcement produced by electrical stimulation of septal area and other regions of rat brain," J. Comp. Physiol. Psychology 47:419-427, 1954).

Additionally, electrical stimulation of nervous tissue of patients has been used to treat addiction and its symptoms. Transcutaneous nerve stimulation has been proposed as a means of relieving the symptoms of withdrawal from an addictive substance (see, for example, U.S. Pat. Nos. 3,946, 745, 4,841,973, 4,865,048, 5,458,625, and 5,593,432). Transcranial electrical fields have been applied to the brain (U.S. Pat. No. 4,646,744) to depolarize nerve cells as a means of treating addictions. The effects of transcranial electrical stimulating fields on withdrawal from addictive substances has been enhanced by the coadministration of a neuroactive chemical promoter (U.S. Pat. No. 5,084,007).

Deep brain stimulation has also been suggested to treat addiction in patients. For example, U.S. Pat. No. 6,109,269 discloses stimulation of multiple sites in the brain to treat addiction in a patient. In the method of U.S. Pat. No. 6,109,269, electrical stimulation using a continuous train of electrical pulses can be employed to excite or inhibit neural activity at a particular stimulation site. For example, high frequency stimulation can be employed to override or block neural activity associated with addiction in a manner similar to the use of high frequency stimulation in Parkinson's Disease to override or block neural activity associated with tremor. U.S. Pat. No. 6,109,269 also discloses combining deep brain stimulation with infusion of various pharmaceutical agents to treat addiction.

SUMMARY

In embodiments of the present disclosure, methods of treating a neurological disorder comprise providing reconditioning electrical stimulation. The methods may comprise applying electrical stimulation that provides positive reinforcement by activation within the reward network of the brain of the patient when an appropriate external or internal stimulus is provided to the patient. The external stimulus is selected in accordance with the specific neurological disorder or other disorder being treated in the patient. The methods may comprise applying electrical stimulation that provides negative reinforcement by stimulation of aversion-related locations of the brain of the patient when a different external or internal stimulus is provided to the patient. Internal stimuli may include gastric contractions, blood glucose levels, blood pressure measurements, heart rate measurements, etc. Accordingly, methods of the present disclosure may include "paired stimulation" of external or internal stimulus with electrical stimulation, or the external/internal stimulus may trigger the electrical stimulation. The duration of the 'pairing' is non-critical, as long as it is consequential. Thus 'pairing' can go from simultaneous, to multiple seconds after the external or internal stimulus.

There are four basic versions of this embodiment: positive reinforcement, negative reinforcement, positive punishment, and negative punishment. These can be combined in different ways, for example positive reinforcement of one external stimulus can be combined with negative reinforcement of another stimulus, or positive punishment of one external stimulus can be combined with negative punishment of another external stimulus. Positive refers to supplying a stimulus to the reward system or antireward system. Negative refers to not supplying (=withholding) a stimulus to the reward or antireward system. Reinforcement is responsible for increasing a behavior, while punishment has the effect of decreasing a behavior In some embodiments of the present disclosure, electrical stimulation is applied to one or more locations within the reward network of the brain of the patient. The reward related locations may include the nucleus accumbens (NAc), the laterodorsal tegmentum, ventral tegmental area (VTA), substantia nigra pars compacta, hypothalamus, the ventral pallidum, the subthalamic nucleus (STN), medial dorsal nucleus of the thalamus, and the posterior cingulate cortex (PCC). In some embodiments, negative feedback may be provided by application of electrical stimulation to one or more aversion related locations (antireward system) in the brain of the patient including the habenula, the rostromedial tegmental nucleus, VTA, the dorsal anterior cingulate cortex (dACC), the dorsolateral prefrontal cortex (DLPFC), and the insula.

In some embodiments, burst stimulation is provided to one or more locations with the brain of the patient in conjunction with the presentation of the respective stimuli. The burst stimulation may comprise respective bursts of multiple electrical pulses. A pulse-repetition rate is defined for the pulses within the respective bursts. Also, an overall or average burst repetition rate may be selected. The burst stimulation effects neurological processes in a manner that differs from conventional tonic stimulation. Many conventional tonic stimulation therapies merely attempt to block "problematic" neuronal activity. Burst stimulation in accordance with embodiments of the present disclosure reconditions neuronal processes for a patient to treat the specific neurological disorder of the patient.

In some embodiments, various forms of addiction are treated using reconditioning electrical stimulation. Although addiction is a neurological disorder appropriate for the therapies described herein, many other neurological disorders may be treated in patients according to the methods of embodiments of the present disclosure. Any neurological or non-neurological pathology that can develop through reinforcement learning, classical or operant conditioning, can be treated by embodiments of the present disclosure.

DETAILED DESCRIPTION

In embodiments of the present disclosure, methods of treating a neurological disorder involve reconditioning one or more neurological processes of a patient. The methods may involve applying electrical stimulation that provides positive reinforcement by activation within the reward network of the brain of the patient when an appropriate external stimulus is provided to the patient. The methods may involve applying electrical stimulation that provides negative reinforcement by stimulation of aversion-related locations of the brain of the patient when a different external stimulus is provided to the patient.

In some embodiments of the present disclosure, electrical stimulation is applied to one or more locations within the reward network of the brain of the patient. The stimulation locations may include the nucleus accumbens (NAc), the laterodorsal tegmentum, ventral tegmental area (VTA), substantia nigra pars compacta, hypothalamus, the ventral pallidum, the subthalamic nucleus (STN), medial dorsal nucleus of the thalamus, and the posterior cingulate cortex (PCC).

In some embodiments, negative feedback may be provided by application of electrical stimulation to one or more aversion related locations in the brain of the patient including the habenula, the rostromedial tegmental nucleus, VTA, the dorsal anterior cingulate cortex (dACC), the dorsolateral prefrontal cortex (DLPFC), and the insula.

In some embodiments, burst stimulation is provided to one or more locations with the brain of the patient in conjunction with the presentation of the respective stimuli. Burst stimulation for neurological reconditioning provides a fundamentally different type of therapy than provided by known therapies involving stimulation of the nucleus accumbens including the therapy of U.S. Pat. No. 6,109,269. In the '239 patent, tonic stimulation is provided that merely attempts to block the "reward" mechanism for substance intake for patients suffering from addiction. In contrast, burst stimulation according to some embodiments of the present disclosure engages the reward circuitry of a patient's brain to reward non-addiction related behaviors or responses. Also, burst stimulation according to some embodiments may stimulate other sites of the patient's brain to activate aversion related neuronal mechanisms for addiction-related behaviors or responses as part of the neurological reconditioning.

Although addiction is a neurological disorder appropriate for the therapies described herein, many other neurological and non-neurological disorders resulting from homeostatic imbalance such as but not limited to hypertension, heart insufficiency, obesity, diabetes mellitus, gout, etc. may be treated in patients according to the methods of embodiments of the present disclosure.

Figure 1:
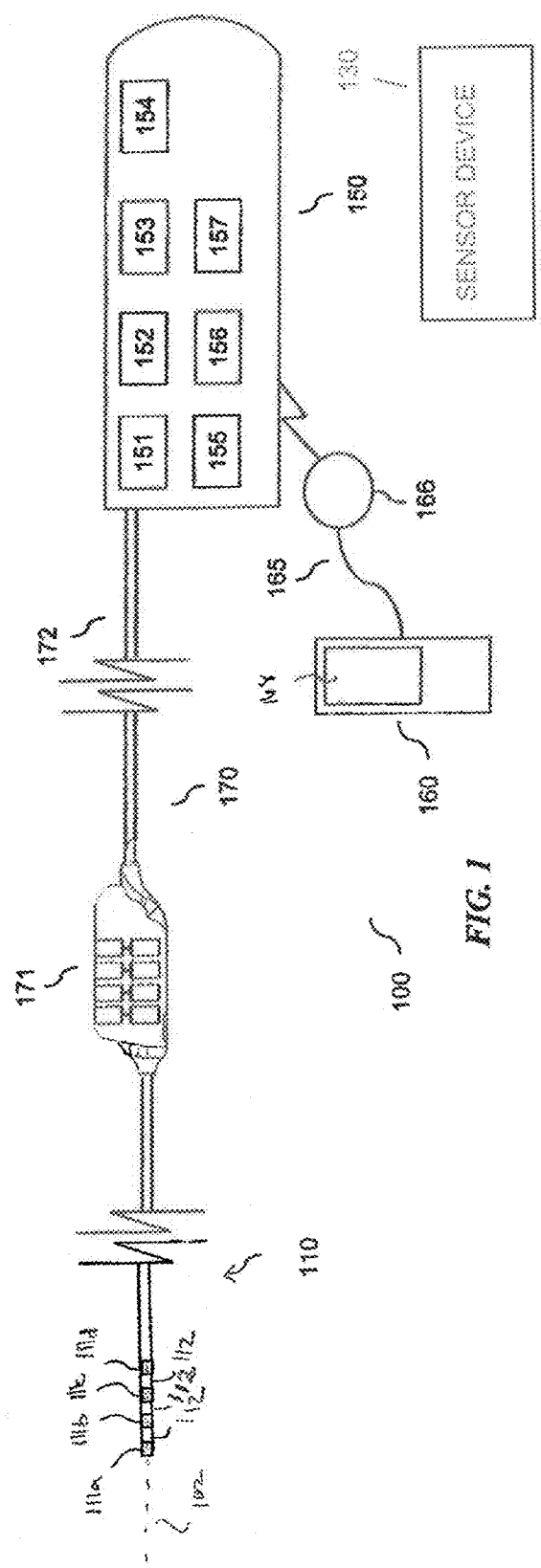
FIG. 1 depicts a neurostimulation system according to representative embodiments of the present disclosure.

FIG. 1 depicts an NS system 100 for providing a reconditioning therapy to a patient according to some embodiments of the present disclosure. NS system 100 includes an implantable pulse generator (IPG) 150 that is adapted to generate electrical pulses for application to tissue of a patient. The IPG 150 typically comprises a metallic housing that encloses a controller 151, pulse generating circuitry 152, a charging coil 153, a battery 154, a far-field and/or near field communication circuitry 155, battery charging circuitry 156, switching circuitry 157, and the like. The controller 151 typically includes a microcontroller or other suitable processor for controlling the various other components of the device. Software code is typically stored in memory of the IPG 150 for execution by the microcontroller or processor to control the various components of the device. An example of a suitable IPG is the BRIO™ implantable pulse generator manufactured by St. Jude Medical, Inc.

IPG 150 may comprise a separate or an attached extension component 170. If the extension component 170 is a separate component, the extension component 170 may connect with the "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150 (through blocking capacitors). Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. Thereby, the pulses originating from the IPG 150 are provided to the leads 110. The pulses are then conducted through the conductors of the lead 110 and applied to tissue of a patient via stimulation electrodes 111a-d. Any suitable known or later developed design may be employed for connector portion 171.

Stimulation electrodes 111a-d may be in the shape of a ring such that each stimulation electrode 111a-d continuously covers the circumference of the exterior surface of the lead 110. Each of the stimulation electrodes 111a-d are separated by non-conducting material 112, which electrically isolate each stimulation electrode 111a-d from an adjacent stimulation electrode 111a-d. The non-conducting material 112 may include one or more insulative materials and/or biocompatible materials to allow the lead 110 to be implantable within the patient. The stimulation electrodes 111a-d may be configured to emit the pulses in an outward radial direction proximate to or within a stimulation target. Additionally or alternatively, the stimulation electrodes 111a-d may be in the shape of a split or non-continuous ring such that the pulse may be directed in an outward radial direction adjacent to the stimulation electrodes 111a-d. Multiple such "segmented" electrodes may be disposed at a given longitudinal position along lead 110 to more finely control application of pulses to one or more neural population(s) during therapeutic operations of NS system 100. Examples of a fabrication process of the stimulation electrodes 111*a-d* is disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is expressly incorporated herein by reference.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 111*a-d* to a plurality of terminals (not shown) of the lead 110. The terminals are adapted to receive electrical pulses and the stimulation electrodes 111*a-d* are adapted to apply the pulses to the stimulation target of the patient. Also, sensing of physiological signals may occur through the stimulation electrodes 111, the conductors, and the terminals. It should be noted that although the lead 110 is depicted with four stimulation electrodes 111*a-d*, the lead 110 may include any suitable number of stimulation electrodes 111*a-d* (e.g., less than four, more than four) as well as terminals, and internal conductors. Additionally or alternatively, various sensors may be located near the distal end of the lead 110 and electrically coupled to terminals through conductors within the lead body 172.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different stimulation electrodes 111*a-d* may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple independent current sources may be employed to provide pulse patterns (e.g., tonic stimulation waveform, burst stimulation waveform) that include generated and delivered stimulation pulses through various stimulation electrodes of one or more leads 111*a-d* as is also known in the art. Various sets of parameters may define the pulse characteristics and pulse timing for the pulses applied to the various stimulation electrodes 111*a-d* as is known in the art. Although constant current pulse generating circuitry is contemplated for some embodiments, any other suitable type of pulse generating circuitry may be employed such as constant voltage pulse generating circuitry.

Controller device 160 may be implemented to charge/recharge the battery 154 of the IPG 150 (although a separate recharging device could alternatively be employed) and to program the IPG 150 on the pulse specifications while implanted within the patient. Although, in alternative embodiments separate programmer devices may be employed for charging and/or programming the NS system 100 and far-field communication may be employed. The controller device 160 may be a processor-based system that possesses wireless communication capabilities. Software may be stored within a non-transitory memory of the controller device 160, which may be executed by the processor to control the various operations of the controller device 160. A "wand" 138 may be electrically connected to the controller device 116 through suitable electrical connectors (not shown). The electrical connectors may be electrically connected to a telemetry component 166 (e.g., inductor coil, RF transceiver) at the distal end of wand 138 through respective wires (not shown) allowing bi-directional communication with the IPG 150. Optionally, in some embodiments, the wand 138 may comprise one or more temperature sensors for use during charging operations. In other embodiments, far field communication circuitry may also be employed to communicate data between IPG 150 and controller device 160.

The user may initiate communication with the IPG 150 by placing the wand 138 proximate to the NS system 104. Preferably, the placement of the wand 138 allows the telemetry system of the wand 138 to be aligned with the far-field and/or near field communication circuitry 155 of the IPG 150. The controller device 160 preferably provides one or more user interfaces 168 (e.g., touchscreen, keyboard, mouse, buttons, or the like) allowing the user to operate the IPG 150. The controller device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different stimulation electrode 111*a-d* combinations.

Also, the controller device 160 may permit operation of the IPG 150 according to one or more stimulation programs to treat the patient. Each stimulation program may include one or more sets of stimulation parameters of the pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 2:
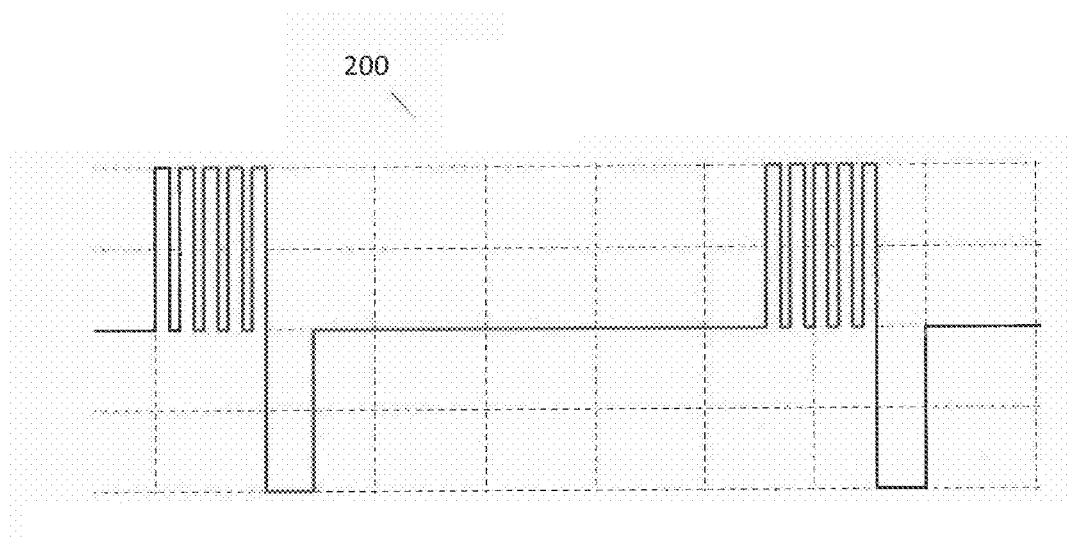
FIG. 2 depicts a burst stimulation pattern for stimulating reward and/or aversion related sites in a patient according to some representative embodiments.

FIG. 2 depicts burst stimulation pattern 200 (e.g., for generation and application to neural tissue of a patient by NS system 100) according to some embodiments of the present disclosure. Burst stimulation pattern 200 includes multiple groups or "bursts" of multiple pulses. A quiescent period is provided between the bursts of pulses. The bursts may be repeated at a suitable rate. The interval between bursts may be varied while maintaining a suitable overall average repetition rate. For example, the inter-burst interval may be psuedo-randomly varied while maintaining an average burst repetition rate.

In some embodiments, a pulse repetition rate is provided for the pulses within a respective burst or group of pulses. The pulse-to-pulse interval within an individual burst may be uniform or varied (e.g., pseudo-randomly). Also, the pulse width may be greater than typically selected for conventional neurostimulation therapies. In some embodiments, longer pulse widths are selected to provide sufficient total charge. Also, charge balancing is preferably not applied within a given burst to permit integration of the applied charge by the stimulated neuronal structures. For example, monophasic (as opposed to charge balanced biphasic) pulses are applied. Charge balancing may occur passively after a given burst is completed. Alternatively, one or more active balancing pulses may be applied after the end of given burst. Although certain specific stimulation rates and parameters are described herein, any suitable rates and parameters may be employed according to some embodiments of the present disclosure.

Electrical stimulation according to some embodiments of this disclosure could be either burst or tonic or clustered high frequency (multiple spikes at e.g. 3 to 50 spikes at 130 Hz), clustered low frequency (multiple spikes at e.g. 3-50 spikes at 20 Hz, 130 Hz, or any other frequency). The difference between burst and clustered firing is that in burst the charge is balanced after the monophasic spikes, whereas in clustered firing each spike is charge balanced (biphasic). Although active balancing is shown in selected drawings, one or more balancing pulses are not required. For example, passive discharge techniques may be applied in lieu of use of balancing pulse of opposite polarity to the burst pulses.

Suitable application of electrical pulses in a burst pattern stimulates neuronal activity that is similar neuronal activity present when physiological burst firing occurs. Burst firing of neurons is typically found in calbindin positive cells (Kawaguchi and Kubota 1993; Hu et al., 1994; Hu 1995; He and Hu 2002). Thus, burst mode firing may utilize a calbindin system to generate the burst. Generally, burst firing is accomplished through the activation of either a subthreshold membrane conductance that initiates action potentials or a suprathreshold membrane conductance that once activated evokes two or more action potentials. Sodium (Na+) and calcium (Ca2+) activated conductances have all been implicated in burst generation. Hippocampal (Wong and Stewart, 1992; Traub et al., 1994) and layer V neocortical (Schwindt and Crill, 1999) pyramidal cells may initiate somatic Na+ action potentials from a slow Ca2+ potential generated within the dendrites. Alternatively, bursts in subicular (Mattia et al., 1997) and sensorimotor cortical neurons (Franceschetti et al., 1995; Guatteo et al., 1996) may be generated through a voltage-dependent Na+ conductance, independent of Ca2+ (Brumberg, 2000).

Burst firing acts in a non-linear fashion (Lisman 1997; Sherman 2001; Swadlow and Gusev 2001) with a summation effect of each spike, thus more readily activating a target cell (Lisman 1997) than tonic firing. Burst firing has been described in drowsiness, slow wave sleep, and anesthesia (Steriade et al., 1989; McCormick and Feeser 1990), as well as epilepsy (Futatsugi and Riviello 1998; Huguenard 1999) in the thalamus, and it functionally shuts off external auditory sensory stimuli to gain access to the cortex (Edeline et al., 2000; Massaux and Edeline 2003; Massaux et al., 2004), though not completely (Edeline et al., 2000). Neural network modeling has further demonstrated that bursts are generated by positive feedback through excitatory connections (Tabak and Latham 2003). In networks of two populations, one excitatory and one inhibitory, decreasing the inhibitory feedback can cause the network to switch from a tonically active, asynchronous state to the synchronized bursting state (van Vreeswijk and Hansel 2001). Additional details of burst stimulation are discussed in U.S. Pat. No. 7,734,340 which is incorporated herein by reference.

Figure 3:
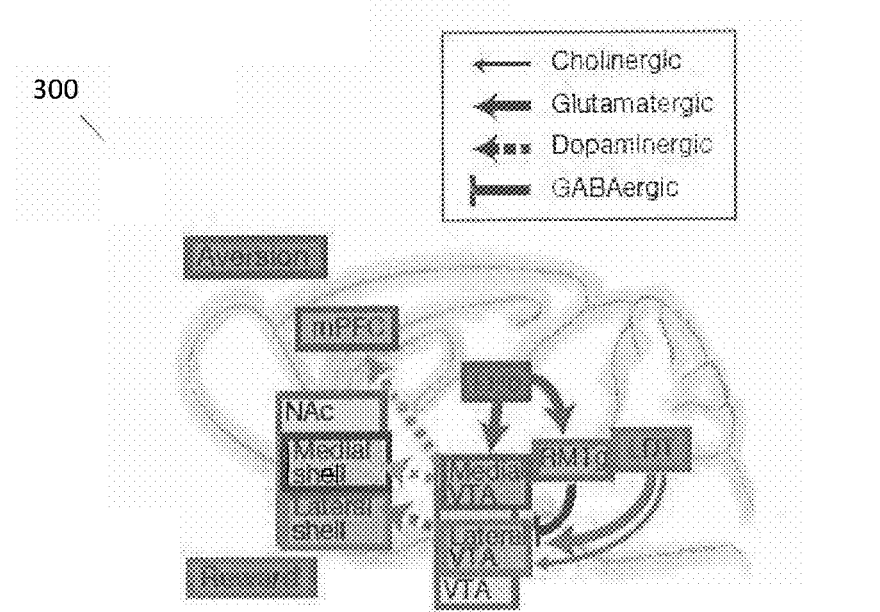
FIGS. 3-10 depict reconditioning therapies according to representative embodiments of the present disclosure.

The ventral tegmentum (VTA) is a population of neurons located close to the midline on the floor of the midbrain (mesencephalon). The VTA is the origin of the dopaminergic cell bodies of the mesocorticolimbic dopamine system. FIG. 3 depicts diagram 300 of some of interconnections between the VTA and other neuronal structures that mediate reward and aversion responses in a patient. Dopaminergic projections from the VTA to the NAc release dopamine in response to reward-related stimuli (and in some cases, aversion-related stimuli). There are also GABAergic projections from the NAc to the VTA; projections through the direct pathway. The NAc also contains numerous types of interneurons. Further, the NAc receives dense innervation from glutamatergic monosynaptic circuits from the medial prefrontal cortex (mPFC), hippocampus (Hipp) and amygdala, as well as other regions. Additionally, the VTA receives such inputs from the lateral dorsal tegmentum (LDTg), lateral habenula and lateral hypothalamus. These various inputs control aspects of reward-related perception and memory. Dopamine neurons emit an alerting message about the surprising presence or absence of rewards. Dopamine neurons in VTA are activated by rewarding events that are better than predicted, remain uninfluenced by events that are as good as predicted, and are depressed by events that are worse than predicted. Further, the nucleus accumbens fires in burst mode and tonic mode where burst neuronal firing encode differences between actual and predicted rewards.

Activation of inputs to the VTA from the laterodorsal tegmentum and the lateral habenula elicit reward and aversion, respectively. Laterodorsal tegmentum neurons preferentially synapse on dopamine neurons projecting to the nucleus accumbens lateral shell, whereas lateral habenula neurons synapse primarily on dopamine neurons projecting to the medial prefrontal cortex as well as on GABAergic neurons in the rostromedial tegmental nucleus. Accordingly, distinct VTA circuits generate reward and aversion for internal and external stimuli.

Also, as used herein, disrewarding means to reverse the act of rewarding; to deprive of reward; to undo a reward, to extinguish a reward (alternatively expressed "antirewarding"). The difference between aversion and disreward is that a disreward does not imply an active punishment. This is relevant as with disrewarding stimuli a patient "unlearns" without punishment. For example, causing distress or disgust with applied stimuli can sometimes be beneficial, e.g. treating disorders involving antisocial, violent, or abusive behaviors. In contrast, disrewarding stimulation removes the predicted reward of the stimulus without aversion. For example, it would be unsuitable to apply aversion stimuli to treat obesity because aversion stimuli may develop anorexia nervosa in patients.

Figure 4:
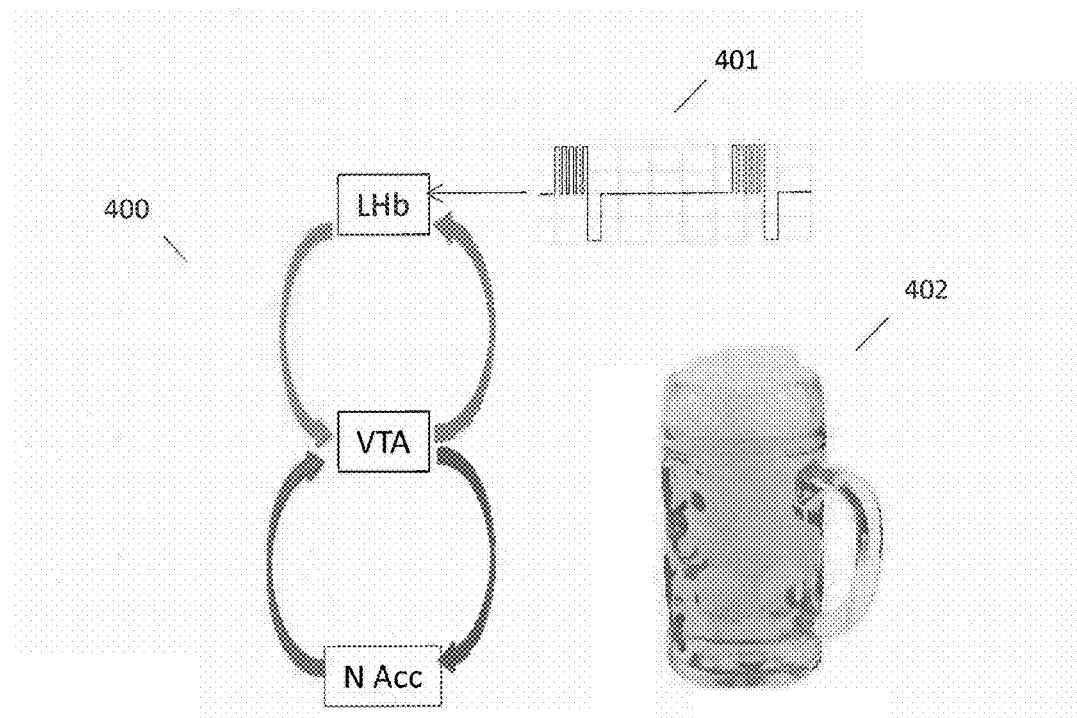

FIG. 4 depicts stimulation therapy 400 according to some embodiments of the present disclosure. Burst stimulation 401 is provided to the lateral habenula (or other aversion related site in the brain) to elicit an aversion response at an appropriate time to recondition a neurological process of the patient. For example, a stimulus may be provided concurrently with application of burst stimulation 401. The stimulus may be selected in accordance with the neurological disorder of the patient. In a patient suffering from addiction, visual stimuli comprising one or more items associated with the patient's specific addiction may be presented to the patient concurrently with application of burst stimulation 401 according to some embodiments of the present disclosure. For example, one or more digital images 402 of alcoholic beverages may be presented to the patient for a patient suffering from addiction. When burst stimulation 401 is applied to the lateral habenula, the resulting input from the lateral habenula to the VTA overrides tonic input from the nucleus accumbens.

Figure 5:
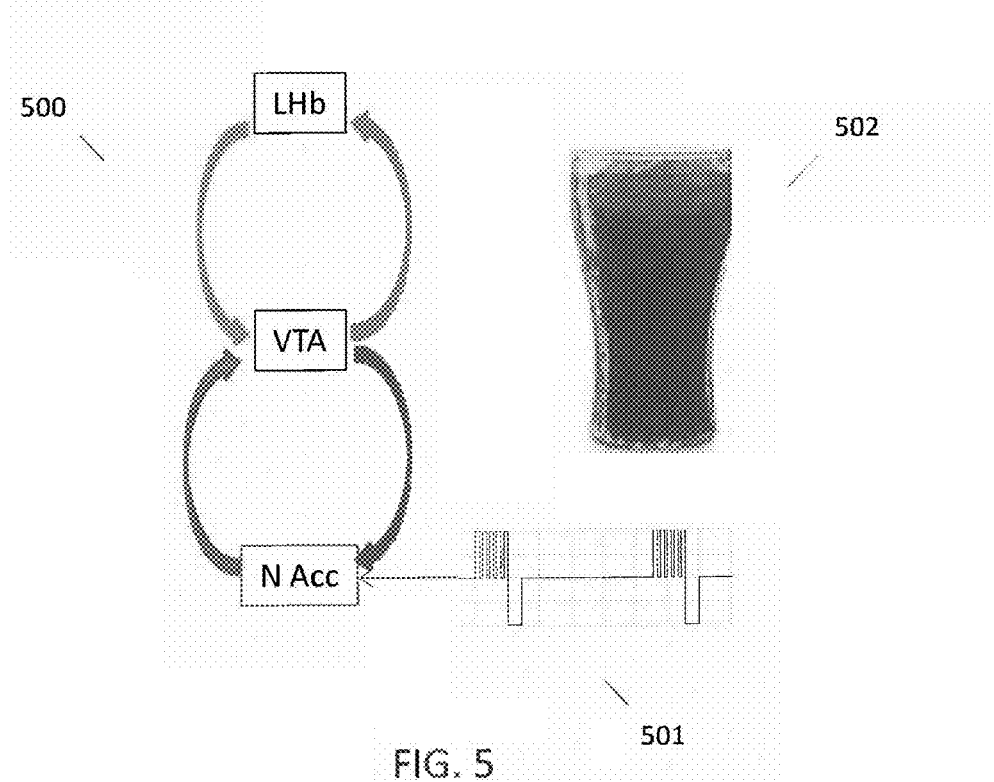

FIG. 5 depicts stimulation therapy 500 according to some embodiments of the present disclosure. Burst stimulation 501 is provided to the nucleus accumbens (or other reward related site in the nervous system) to elicit a reward response at an appropriate time to recondition a neurological process of the patient. Burst stimulation 501 may be provided concurrently with application or presentation of external stimuli, such as presentation of one or more digital images 502. The stimuli selected for presentation with the rewarding burst stimulation 501 will differ from the stimuli selected for the aversion eliciting burst stimulation 401. For example, the stimuli selected for burst stimulation 501 may include presentation of images of one or more items for reinforcement of healthy, non-addiction related behaviors. When burst stimulation 501 is applied to the nucleus accumbens, the resulting input from the nucleus accumbens to the VTA overrides tonic input from the lateral habenula.

Figure 6:
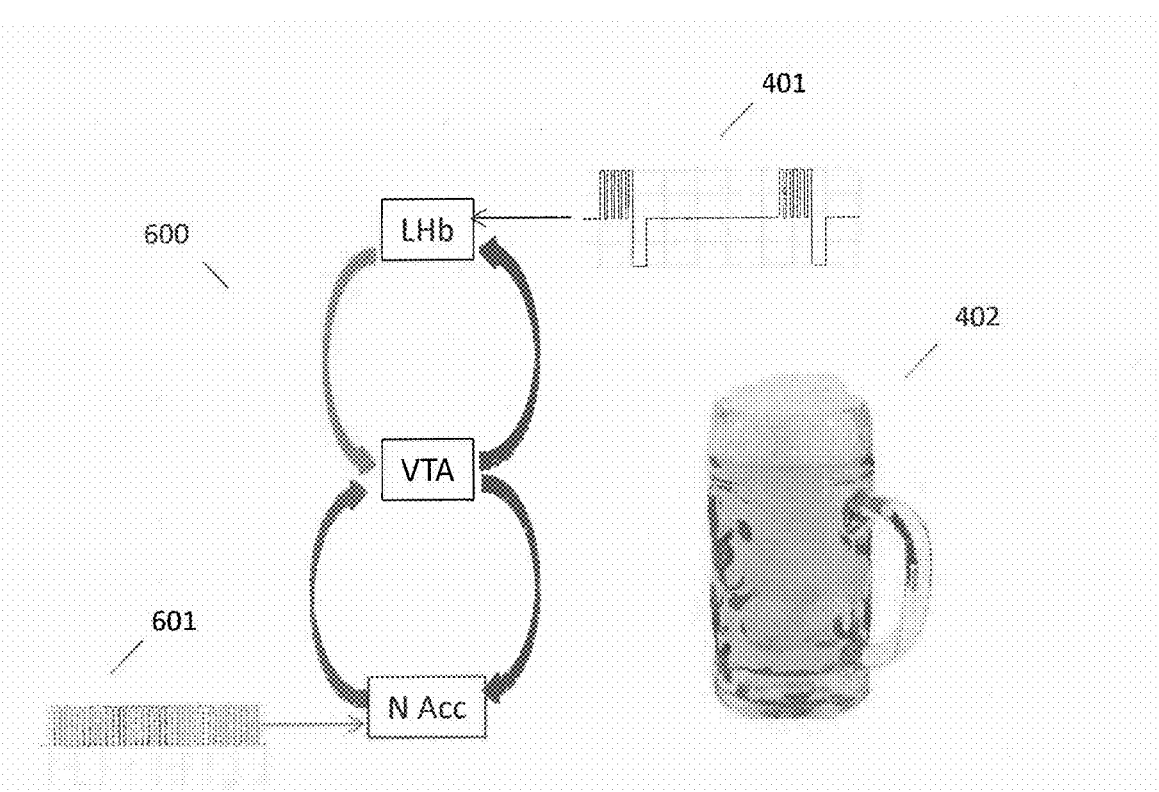

FIG. 6 depicts therapy 600 according to some embodiments. Therapy 600 is similar to therapy 400 except high frequency stimulation 601 (e.g., approximately 100 Hz or greater) is provided to the nucleus accumbens while burst stimulation 401 is provided to the lateral habenula. The high frequency stimulation is preferably provided as charge balanced tonic pulses. Stimulation 601 blocks activity of the nucleus accumbens from providing input to the VTA while input from the lateral habenula to the VTA occurs (as a result of burst stimulation 401).

Figure 7:
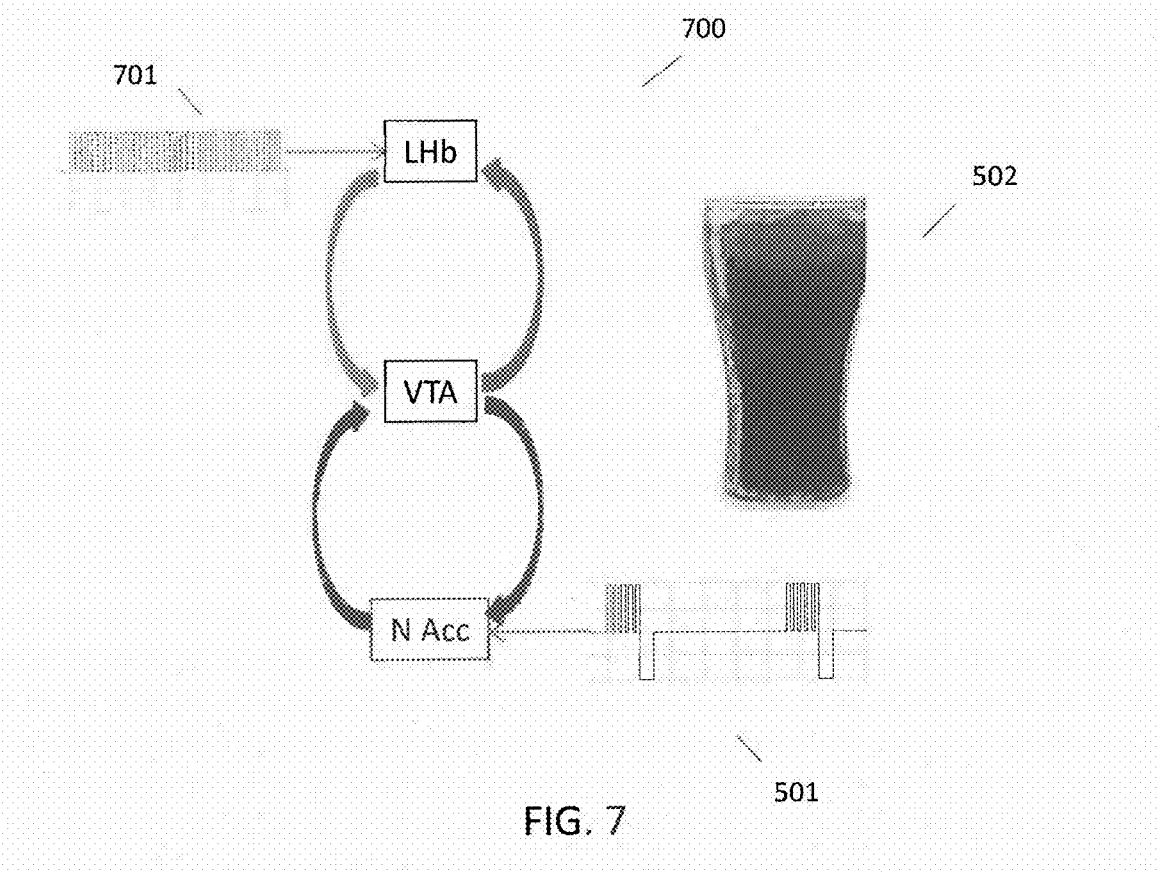

FIG. 7 depicts therapy 700 according to some embodiments. Therapy 700 is similar to therapy 500 except high frequency stimulation 701 (e.g., approximately 100 Hz or greater) is provided to lateral habenula the while burst stimulation 501 is provided to the nucleus accumbens. The high frequency stimulation is preferably provided as charge balanced tonic pulses. Stimulation 701 blocks activity of the lateral habenula from providing input to the VTA while input from the nucleus accumbens to the VTA occurs (as a result of burst stimulation 501).

Figure 8:
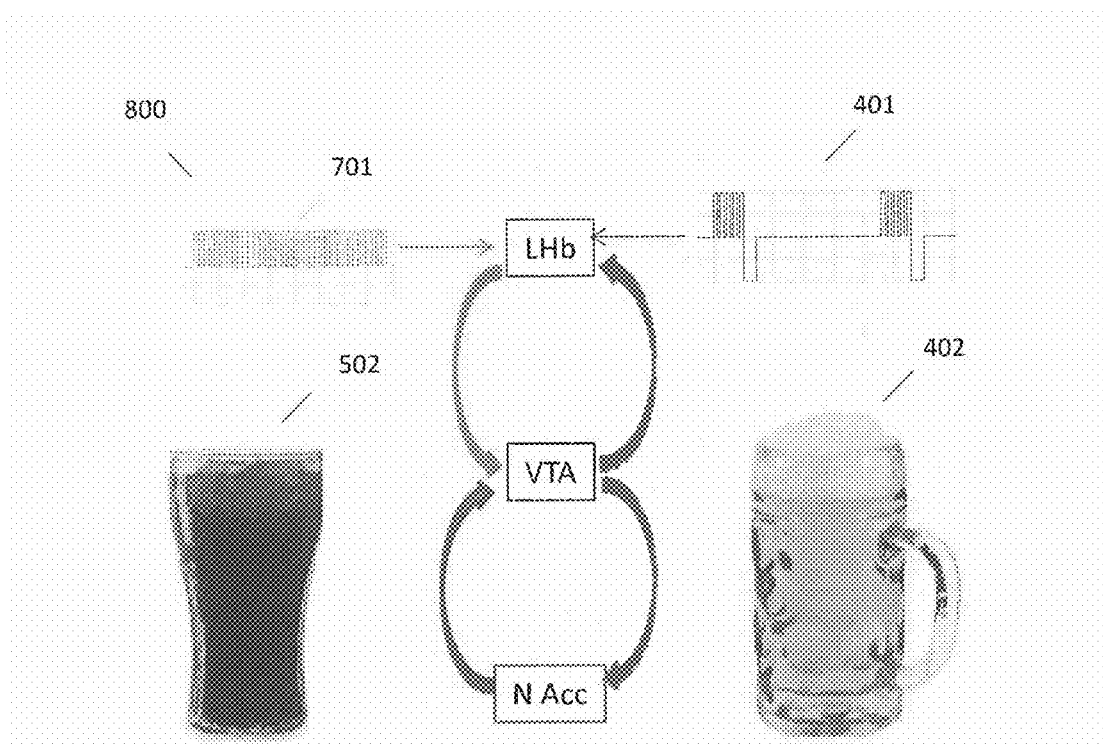

FIG. 8 depicts therapy 800 according to some embodiments of the present disclosure. At time $T_1$, high frequency stimulation 701 (e.g., approximately 100 Hz or greater) is provided to the lateral habenula while an external stimulus is provided to the patient. For example, one or more digital images 502 may be presented to the patient. At time $T_2$, burst stimulation 401 is provided to the lateral habenula (or other aversion related site in the brain) while an external stimulus 402 is provided concurrently.

Figure 9:
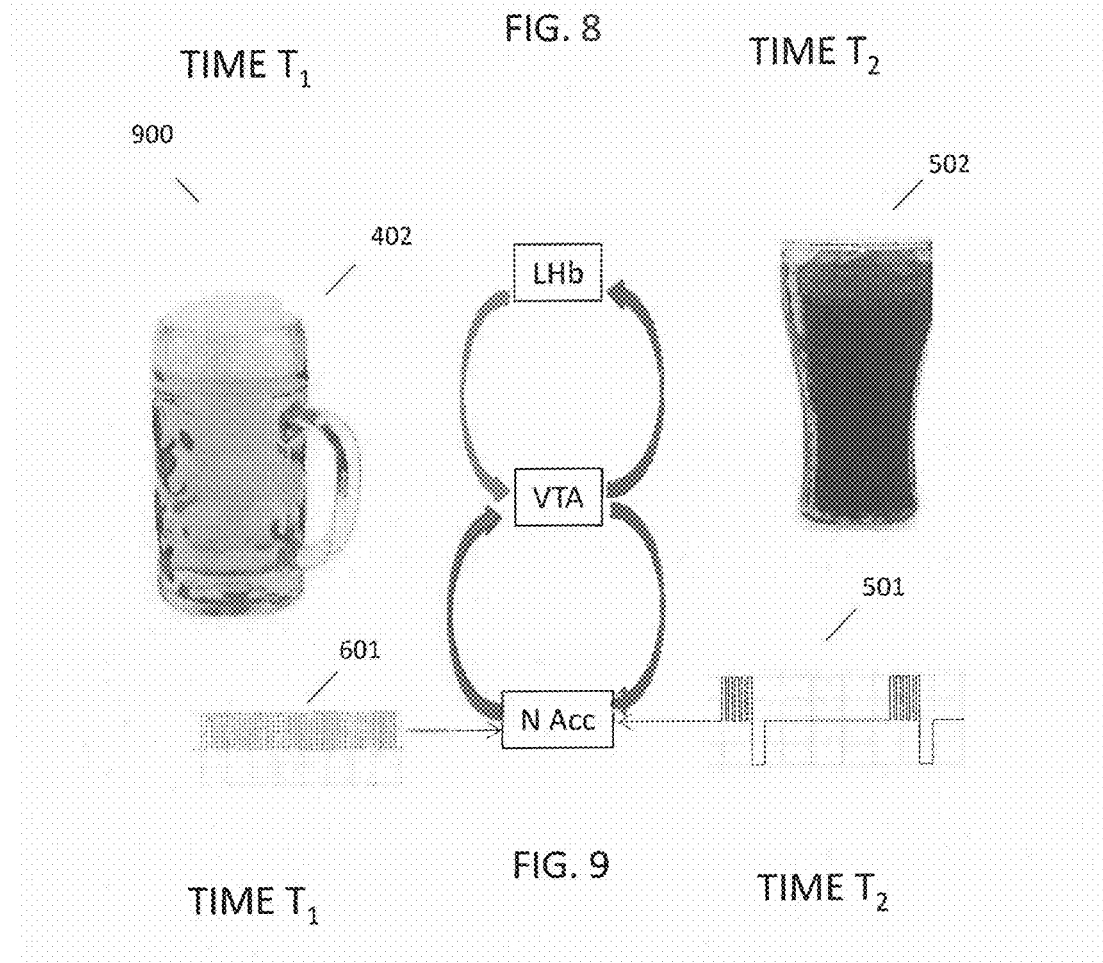

FIG. 9 depicts therapy 900 according to some embodiments of the present disclosure. At time $T_1$, high frequency stimulation 601 (e.g., approximately 100 Hz or greater) is provided to the nucleus accumbens while an external stimulus is provided to the patient. For example, one or more digital images 402 may be presented to the patient. At time $T_2$, burst stimulation 501 is provided to the nucleus accumbens while an external stimulus (one or more digital images 502) is provided concurrently.

In some embodiments, multiples stimulation therapies (including therapies 400, 500, 600, 700, 800, and 900) are provided to a patient at respective times to treat a neurological disorder in the patient. Also, one or more of the respective therapies may be repeated over time as deemed appropriate by the patient's physician during a course of treatment.

Although the nucleus accumbens and the lateral habenula are discussed in regard to FIGS. 4-9, other suitable stimulation sites may be alternatively applied for the reward and aversion related mechanisms according to embodiments of the present disclosure. The reward-related stimulation locations may include the nucleus accumbens (NAc), the laterodorsal tegmentum, ventral tegmental area (VTA), the ventral pallidum, the subthalamic nucleus (STN), medial dorsal nucleus of the thalamus, and the posterior cingulate cortex (PCC). Aversion-related stimulation sites may include the habenula, the rostromedial tegmental nucleus, VTA, amygdala, the dorsal anterior cingulate cortex (dACC), the dorsolateral prefrontal cortex (DLPFC), and the insula.

Although some embodiments employ tonic and/or burst and/or clustered firing stimulation, other stimulation patterns may be provided to the respective stimulation sites described herein. Neurological diseases, treated according to some embodiments, are often characterized by increased functional connectivity. In such embodiments, the discussed neurological disorder/diseases are treated by application of noise stimulation tb one or more stimulation locations identified in this application. In some specific embodiments, the noise stimulation is limited to a specific frequency band. The noise stimulation may be implemented by irregular (in the time domain) application of pulses accord to a single pulse repetition frequency.

In some embodiments, noise stimulation and/or irregular stimulation may be applied within frequency bands of various bandwidths, e.g. 2 Hz bandwidth (1-2 Hz, 2-3 Hz, 3-4 Hz etc), 3 Hz bandwidth (1-3 Hz, 2-4 Hz, 3-5 Hz etc.), 4 Hz bandwidth, 5 Hz bandwidth etc. In one specific embodiment, noise stimulation is applied within one or more of the classical frequency bands, delta (1-4 Hz), theta (4-7 Hz), alpha (8-12 Hz), beta (13-30 Hz) and gamma (30-100 Hz). The classical frequency bands for the purpose of noise stimulation according to some embodiments, can be further subdivided into alpha1 (8-10 Hz), alpha2 (10-12 Hz), Low Beta Waves=beta1 (12.5-16 Hz); Beta Waves=beta2 (16.5-20 Hz); and High Beta Waves=beta3 (20.5-28 Hz). The beta band may be subdivided into 5 bands for noise stimulation according to some embodiments. Gamma waves can also be subdivided in different subgroups: low gamma (30-50 Hz), mid gamma (50-70 Hz) and high gamma (70-100 Hz). There are also specific bands related to sensory and motor processing, e.g. SMR (sensorimotor rhythm): (12.5-15.5 Hz), Mu wave: (7.5-12.5 Hz). The bandwidth groups for stimulation according to some embodiments may begin at any suitable level, for example, at 0.5 or other levels (0.1, 0.2, 0.3 etc).

Noise stimulation within a given bandwidth may be selected to possess a suitable power density or spectral profile. For example, the spectral profile may be possess one of the following power densities or spectral profiles: white) ($1/f^0$), pink ($1/f$), brown ($1/f^2$) or black ($1/f^3$), i.e. $1/f^\beta$ with $\beta=0$ to 10, usually $\beta=0$ or 1 or 2 or 3 or somewhere in between e.g. 0.9, 1.1, etc. Additionally, details of creating a suitably shaped noise signal are discussed in U.S. Pat. No. 8,682,441 which is incorporated herein by reference.

In some embodiments, the noise stimulation is applied to jam or disrupt ongoing connectivity frequency-specific (or frequency band-specific information) transmission between different areas of the nervous system so that hyperconnectivity is blocked or normal connectivity is maintained. By employing stimulation at suitable stimulation sites, there will be no cross-frequency coupling possible on this irregular, noisy frequencies, or frequency bands.

Figure 10:
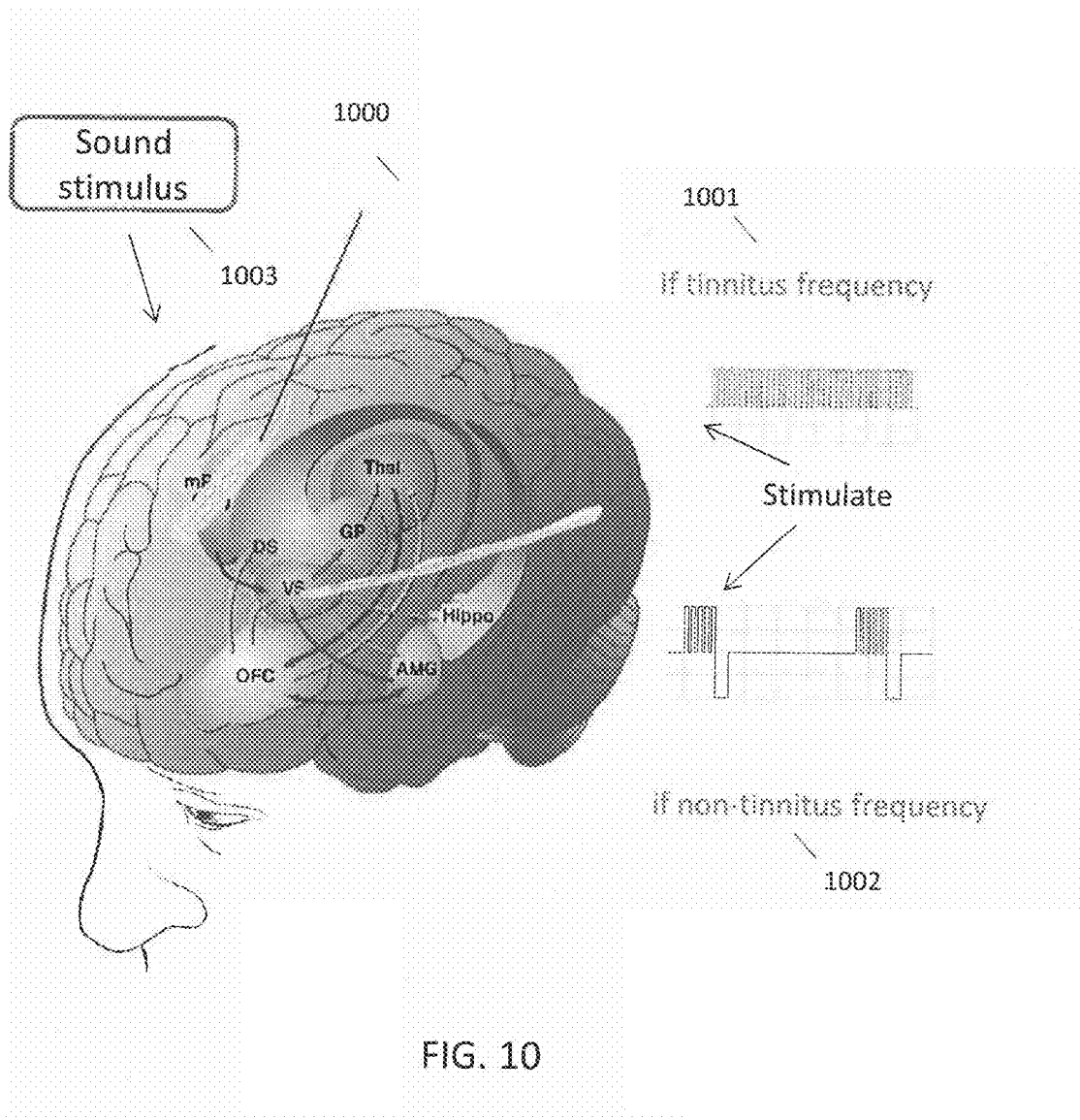

Although addiction related disorders have been discussed, many neurological disorders may be treated using reconditioning stimulation according to some embodiments of the present disclosure. For example, FIG. 10 depicts recondition therapy 1000 for treating tinnitus in a patient. Tinnitus is often described as perception of a "ringing" sound within the human ear when no actual sound is present. The neurological disorder of tinnitus is described in U.S. Pat. No. 7,315,761 which is incorporated herein by reference. Often, tinnitus is caused by a lesion or damage within the auditory tract, caused by a sound trauma or the use of particular antibiotics as examples. Neuroplasticity occurs in response to the lesion or damage and affects the cells related to the frequency or frequencies associated with the lesion. Tinnitus generally occurs as a result from the neuroplastic cortical reorganization. In severe cases, the patient's experience of tinnitus is similar to chronic pain and the patient's tinnitus negatively impacts many activities of the patient.

In therapy 1000, sound stimulus 1003 is provided to the patient. The sound stimulus is provided at a specific frequency. At a given time, the frequency is at the tinnitus frequency of the patient. Upon presentation at the tinnitus frequency, a high frequency blocking pulse train 1001 is provided to an appropriate reward-related site (e.g., as identified herein) in the brain of the patient. The application of pulses may occur using cortical or deep brain stimulation depending upon the selected location. At another given time, the frequency of sound stimulus 1003 is selected to be a frequency different from the tinnitus frequency of the patient. During this presentation of sound stimulus 1003, burst stimulation 1002 is provided to the patient at an appropriate reward-related location site within the brain of the patient. The presentation of the various sound frequencies and application of electrical pulses reconditions neuronal processes within the brain of the patient to treat the patient's tinnitus. Appropriate electrical stimulation may additionally or alternatively be provided to one or more aversion-related sites (e.g., as identified herein) upon presentation of tinnitus frequency and non-tinnitus frequency stimuli as discussed herein.

In some representative embodiments, burst parameters are selected by analyzing neuronal activity that occurs in response to presentation of stimuli to the patient. Neuronal activity is measured using one or more electrodes implanted in the respective reward/aversion sites. For a patient suffering from addiction, one or more addiction-related stimuli (e.g., image 402) are presented to the patient. Neuronal activity is recorded in, for example, the nucleus accumbens. The neuronal activity is processed to identify neuronal spiking and the timing of identified neuronal spikes are employed to select the timing of pulses within the burst pattern. Specifically, the burst frequency and the pulse rate within an individual burst may be selected according to the recorded neuronal activity. The determined pulse parameters are then employed to provide reconditioning stimulation for presentation of non-addiction related stimuli. In this case, image 502 may be presented to the patient and burst stimulation according to the determined parameters is simultaneously applied to the nucleus accumbens. In an alternative embodiment, neuronal activity is detected using a suitable recording electrode, digital samples of the amplitude of the neuronal activity are stored, and the digital samples are subsequently applied as electrical stimulation to the target site (e.g., stimulation pulses proportional to or otherwise corresponding to the record amplitudes) for a reconditioning therapy. Similar sampling and stimulation using either of these techniques may be employed to record reward responses and subsequently to elicit aversion response to addiction-related or other stimuli by stimulation of a suitable aversion related site using the derived or recorded stimulation pattern.

Referring again to FIG. 1, reconditioning stimulation may be applied by detection of addiction related items, environments, or substances using one or more sensors. Different sensors may be employed depending upon the applied method for detecting whether recondition stimulation is appropriate. As shown in FIG. 1, external sensor device 130 is provided. Sensor device 130 includes sensing capabilities and is capable of communicating with one or both of controller device 160 and IPG 150 (e.g., using wireless communication circuitry). Sensor device 130 could be a smart "wearable" device. One example is a wearable system of a computer, an optical head-mounted display, and camera (including the GOOGLE GLASS™ from Google, Inc.). In this case, sensor device 130 could be programmed to capture images of the patient's environment from time to time. Upon applying an image processing, pattern matching analysis, and/or the like, sensor device 130 may communicate a signal (for example, either to IPG 150 or controller device 160) to apply appropriate stimulation to the patient. For example, image processing may be applied to detect product labeling, product shapes, bar codes, and/or the like corresponding to addiction-related products and non-addiction related products. Depending upon detection of a relevant item, suitable reward or aversion eliciting stimulation may be applied as discussed herein.

In other embodiments, sensor device 130 is adapted to obtain physiological data. Sensor device 130 may be implemented as a smart watch and may include one or more physiological sensors. For example, sensors may be provided to measure body temperature, heart rate and heart rate variability, blood oxygen levels, blood pressure, muscle (striated, smooth, and/or cardiac) activity, blood glucose levels, electrolytes, hormones, cytokines, neurotransmitters, neuromodulators, and electrical activity from the central (brain, brainstem, spinal cord) or peripheral and autonomic (sympathetic and parasympathetic) nervous system. The sensor of electrical brain activity can record single cell activity or local field potentials (multiple cell activity) and use amplitude, phase or frequency (discrete frequencies or frequency bands) as a basis to activate the IPG. The IPG may process data from the at least one sensor to analyze amplitude, phase, or frequency characteristics of the neuronal activity to control stimulation. The IPG may employ suitable signal processing algorithms including windowing, discrete cosine transfer (DCT), fast fourier transform (FFT), etc.

Two or more sensors may be employed to detect functional (correlated activity) or effective (directional correlated activity) connectivity. In some embodiments, the correlated activity can be frequency or frequency-band specific or cross-frequency correlated in which different frequencies or frequency bands are coupled. In some embodiments, the IPG detects neural coupling activity based on correlations between one combination of neural activity characteristics from two different sites selected from the list consisting of: phase and amplitude, phase and power, phase and phase, amplitude and amplitude, power and power, phase and frequency, amplitude and frequency, and frequency and frequency.

In some embodiments, these various physiological signals may be correlated to intake of addiction-related substances and suitable stimulation may be provided in response to identified measurements of these signals. In alternative embodiments, IPG 150 may be connected to implantable sensors to control application of stimulation. For example, the patient's blood alcohol level may be measured using an implantable sensor to control the application of reconditioning stimulation by IPG 150.

The controllers and devices discussed herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers and devices discussed herein may include circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers and devices discussed herein may execute a set of instructions that are stored in one or more storage elements, in order to process data. The storage elements may also store data or other information as desired or needed. The storage element may be in the form of an information source or a physical memory element within the controllers and devices discussed herein. The set of instructions may include various commands to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

The invention claimed is:

1. A method of treating a neurological disorder in a patient, comprising:
   providing one or more external stimuli to the patient relevant to the patient's neurological disorder, wherein the one or more external stimuli comprises visual stimuli related to the neurological disorder of the patient; and
   concurrently with providing the one or more external stimuli, electrically stimulating one or more locations in a brain of the patient to elicit a reward-response to the one or more external stimuli, to elicit a disreward response, or to elicit an aversion-response to the one or more external stimuli, wherein the electrically stimulating provides electrical pulses to the one or more locations in the brain of the patient for a time period limited to 2.5 seconds or less.

2. The method of claim 1 wherein the electrically stimulating comprising:
   applying electrical pulses according to a burst pattern of multiple bursts separated by quiescent intervals with each burst of the burst pattern comprising multiple electrical pulses or clustered firing.

3. The method of claim 1 further comprising
   providing a first external stimulus for presentation concurrently with electrical stimulation of a reward-related location within the brain of the patient.

4. The method of claim 3 wherein the reward-related location is selected from the list consisting of: the nucleus accumbens (NAc), the laterodorsal tegmentum, ventral tegmental area (VTA), substantia nigra pars compacta, hypothalamus, the ventral pallidum, the subthalamic nucleus (STN), medial dorsal nucleus of the thalamus, and the posterior cingulate cortex (PCC).

5. The method of claim 3 further comprising:
   providing a second external stimulus for presentation concurrently with electrical stimulation of a disrewarding/antirewarding or aversion-related location within the brain of the patient.

6. The method of claim 5 wherein the disrewarding/antirewarding or aversion-related location is selected from the list consisting of: the habenula, the rostromedial tegmental nucleus, ventral tegmental area (VTA), the amygdala, the dorsal anterior cingulate cortex (dACC), the dorsolateral prefrontal cortex (DLPFC), and the insula.

7. The method of claim 1 wherein the neurological disorder is an addiction or substance use disorder.

8. The method of claim 1 wherein the neurological disorder is an eating disorder.

9. The method of claim 1 wherein the neurological disorder is an auditory disorder.

10. The method of claim 9 wherein the auditory disorder is tinnitus.

11. The method of claim 1 wherein the neurological disorder is chronic pain.

12. The method of claim 1 wherein the neurological disorder is selected from the list consisting of depression, bipolar disorder, post-traumatic stress disorder (PTSD), panic disorder, phobia, schizophrenia, psychopathy, and antisocial personality disorder.

13. The method of claim 1 wherein the neurological disorder is a reward deficiency syndrome.

14. The method of claim 13 wherein the neurological disorder is an addictive disorder.

15. The method of claim 14 wherein the addictive disorder is selected from the list consisting of alcohol abuse, substance abuse, smoking, and obesity.

16. The method of claim 13 wherein the neurological disorder is an impulsive disorder.

17. The method of claim 16 wherein the impulsive disorder is selected from the list consisting of attention deficit hyperactivity disorder (ADHD), Tourette's syndrome, and autism.

18. The method of claim 13 wherein the neurological disorder is a compulsive disorder.

19. The method of claim 18 wherein the compulsive disorder is selected from the list consisting of obsessive compulsive disorder (OCD), gambling, and aberrant sexual behavior.

20. The method of claim 13 wherein the neurological disorder is a personality disorder.

21. The method of claim 20 wherein the personality disorder is selected from the list consisting of conduct disorder, antisocial personality, and aggressive behavior.

22. The method of claim 1 wherein the one or more external stimuli comprise one or more images.

23. The method of claim 1 wherein the one or more external stimuli comprise one or more images of items relevant to an addiction of the patient.

24. The method of claim 1 wherein the one or more external stimuli comprise auditory, visual, somatosensory, olfactory, vestibular, emotional or cognitive stimuli.

25. The method of claim 1 wherein the one or more external stimuli comprise a first auditory stimulus at a first frequency and a second auditory stimulus at a second frequency, wherein the first and second frequencies are different, and the first frequency is selected to correspond to a tinnitus frequency of the patient.

26. The method of claim 1 further comprising:
detecting one or more items in an external environment of the patient that correspond to a patient's addiction; and
applying electrical stimulation of at least one of a reward-related site and an aversion-related site in the patient's brain.

27. The method of claim 1 further comprising:
detecting one or more physiological signals of the patient that correspond to the neurological disorder; and
applying electrical stimulation of at least one of a reward-related site and an aversion-related site in the patient's brain.

* * * * *